United States Patent
Ishikawa et al.

(10) Patent No.: US 6,519,491 B2
(45) Date of Patent: Feb. 11, 2003

(54) BIO-CHARACTERISTIC VALUE MEASURING APPARATUS WITH SIMPLIFIED SETTING AND DISPLAY RECOGNITION

(75) Inventors: Toshihiko Ishikawa, Tokyo (JP); Kazuyasu Koyama, Tokyo (JP); Hiroki Kenmochi, Fuchu (JP)

(73) Assignee: Tanita Corporation, Tokyo (JP)

( * ) Notice: Subject to any disclaimer, the term of this patent is extended or adjusted under 35 U.S.C. 154(b) by 23 days.

(21) Appl. No.: 09/769,419

(22) Filed: Jan. 26, 2001

(65) Prior Publication Data

US 2001/0011043 A1 Aug. 2, 2001

(30) Foreign Application Priority Data

Jan. 31, 2000 (JP) .......................................... 2000-021406

(51) Int. Cl.[7] .............................. A61B 5/05; A61B 5/00; G06F 17/00
(52) U.S. Cl. ..................... 600/547; 600/300; 128/920
(58) Field of Search ................ 600/547, 300; 128/920, 921

(56) References Cited

U.S. PATENT DOCUMENTS

| | | | | |
|---|---|---|---|---|
| 4,796,182 A | * | 1/1989 | Duboff | 128/921 |
| 5,372,141 A | * | 12/1994 | Gallup et al. | 600/547 |
| 5,796,640 A | * | 8/1998 | Sugarman et al. | 128/921 |
| 6,066,105 A | * | 5/2000 | Guillen | 600/595 |
| 6,129,663 A | * | 10/2000 | Ungless et al. | 600/300 |
| 6,314,405 B1 | * | 11/2001 | Richardson | 600/300 |

* cited by examiner

Primary Examiner—Max F. Hindenburg
Assistant Examiner—Navin Natnithithadha
(74) Attorney, Agent, or Firm—McDermott, Will & Emery

(57) ABSTRACT

A bio-characteristic value measuring apparatus is provided, comprising an input device, a storage device, a measuring device, an arithmetic and control device, and a display device. The input device inputs a personal body data of a test subject; the storage device stores the inputted personal body data; the measuring device measure a physical characteristics of a living body; the arithmetic and control device evaluates a condition of the living body of the test subject based on the physical characteristics and the inputted personal body data; and the display device indicates the inputted personal body data and evaluated result. Upon setting the personal body data, a luminescent element in the input device corresponding to a section available for an entry operation is lighted up.

9 Claims, 7 Drawing Sheets

BIO-CHARACTERISTIC VALUE MEASURING APPARATUS WITH SIMPLIFIED SETTING AND DISPLAY RECOGNITION

FIELD OF THE INVENTION

The present invention relates to a setting and display method of an apparatus for measuring a physical-characteristic value of a living body, and in particular, to a method of setting and displaying a personal body data of a body fat meter for measuring a body fat percentage or a body fat mass based on the bioelectric impedance method.

DESCRIPTION OF THE PRIOR ART

In recent years, there is a growing awareness of the fitness, and it has led to a variety of devices provided and used for evaluating a various data, such as blood pressure and pulse, concerning to a human body of user. In particular, there seems to be a trend toward an idea to set a higher value on a body fat percentage than a body weight in health care. Accordingly, a body fat meter has been suggested which takes advantage of the fact that the body fat mass of a human body could be evaluated by using a bioelectric impedance, and because of its simplicity in a measurement, a variety of commercial products employing this device has become widely used at home. It has become to be generally recognized that a person with higher body fat percentage has a higher risk to suffer from adult disease, and in these days more health-conscious folks, without regard to the young or the old, have commonly checked the body fat thereof by using those body fat meters. Further, a body fat meter including an integrated body weight scale also has been getting popular to support the health care in both viewpoints of body weight and body fat percentage.

These body fat meter described above applies an current into a body of a test subject through end portions thereof to measure a voltage between these sites thus to measure a bioelectric impedance value. Based on this obtained impedance value and a set of personal body information, such as the height, the weight, the sex and the age of the test subject, the body fat meter evaluates a current body fat percentage or a body fat mass, a weight of the body fat, to be indicated.

As described above, since the body fat meter uses a set of personal body information, such as the height, the weight, the sex and the age of the test subject for evaluation, the data is required to be inputted to the device. On this purpose, the test subject using the body fat meter uses a set switch to set the personal body information including the height, the weight, the sex and the age of the subject in order. Further, in the body fat meter including the integrated body weight scale, since the measured body weight value is directly used to evaluate a body fat percentage, the body weight is not required to be set in advance, but the other data should be required to do so.

Further, a body fat meter used at home is driven by using batteries, and if the body fat meter is left in displaying state for a long time after the switch is pressed, it consumes the current in vain to result in the need for a frequent exchange of batteries. To prevent this problem, the bio-characteristic value measuring apparatus is usually equipped with an automatic power-off function for automatically turning off the power supply in such case that no entry has occurred for a certain period, thus making the battery life longer.

However, there must be a case that a user of a bio-characteristic value measuring apparatus is an elderly person who is probably inexperienced in machine operation. In such case, sometimes a trouble has happened that a function of automatic power-off becomes activated to turn off the power supply in the course of setting while the user keeps on setting with referring to the instruction. Due to this, disadvantageously there has been a probability that, for example, the user is prohibited from completing the setting or the user uses the body fat meter with improper setting to measure a body fat percentage, resulting in an improper health management.

Further, the automatic power-off function is also activated during the measuring operation of the bio-characteristic value measuring apparatus so as to automatically turn off the power supply a few seconds after a certain time period of result display. However, this automatic power-off function has been typically set to a certain time period, with regardless to the differences among the users, for example, a difference between a user capable of making a quick recognition of the display contents and an elderly user with weak eyesight or poor thinking faculty, and some users have thought that the display period is rather shorter, because the display has happened to disappear while they are struggling with recalling the formerly measured value.

The present invention is made in the light of these problems described above, and accordingly an object thereof is to provide an improve bio-characteristic value measuring apparatus which allows a user to set his (her) personal body data with easier manner taking sufficient time, and also allows to use the apparatus more easily by modifying a display period of a result in response to the request of the user.

SUMMARY OF THE INVENTION

In accordance with an aspect of the present invention, a bio-characteristic value measuring apparatus comprises an input device, a storage device, a measuring device, an arithmetic and control device, and a display device, in which:

said input device inputs a personal body data of a test subject;

said storage device stores said inputted personal body data;

said measuring device measures a physical characteristics of a living body;

said arithmetic and control device evaluates a condition of the living body of the test subject based on said physical characteristics and said inputted personal body data; and said display device indicates the inputted personal body data and evaluated result and the likes;

wherein in said input device, upon setting the personal body data, a luminescent element corresponding to a section available for an entry operation is lighted up.

In accordance with another aspect of the present invention, a bio-characteristic value measuring apparatus comprises an input device, a storage device, a measuring device, an arithmetic and control device, and a display device, in which:

said input device inputs a personal body data of a test subject;

said storage device stores said inputted personal body data;

said measuring device measures a physical characteristics of a living body;

said arithmetic and control device evaluates a condition of the living body of the test subject based on said physical characteristics and said inputted personal body data; and said display device indicates the inputted personal body data and evaluated result and the likes;

wherein in said input device, upon setting the personal body data, a luminescent element corresponding to a section available for an entry operation is lighted up; and said display device, upon setting the personal body data, indicates a data available for an entry operation.

In accordance with yet another aspect of the present invention, a bio-characteristic value measuring apparatus comprises an input device, a storage device, a measuring device, an arithmetic and control device, and a display device, in which:

said input device inputs a personal body data of a test subject including an age data;

said storage device stores said inputted personal body data;

said measuring device measures a physical characteristics of a living body;

said arithmetic and control device evaluates a condition of the living body of the test subject based on said physical characteristics and said inputted personal body data; and said display device indicates the inputted personal body data and evaluated result and the likes;

wherein said arithmetic and control device modifies a standby time until an automatic power-off based on the entered age data.

In accordance with yet another aspect of the present invention, a bio-characteristic value measuring apparatus comprises an input device, a storage device, a measuring device, an arithmetic and control device, and a display device, in which:

said input device inputs a personal body data of a test subject including an age data;

said storage device stores said inputted personal body data;

said measuring device measures a physical characteristics of a living body;

said arithmetic and control device evaluates a condition of the living body of the test subject based on said physical characteristics and said inputted personal body data; and said display device indicates the inputted personal body data and evaluated result and the likes;

wherein in said input device, upon setting the personal body data, a luminescent element corresponding to a section available for an entry operation is lighted up; and said arithmetic and control device modifies a standby time until an automatic power-off based on the entered age data.

Yet further, in a bio-characteristic value measuring apparatus according to the present invention, the data to be inputted first among the personal body data from said input device is a data concerning to the age.

Still further, a bio-characteristic value measuring apparatus according to the present invention, said arithmetic and control device modifies the standby time until the automatic power-off to become longer as the entered age gets higher.

Still further, in a bio-characteristic value measuring apparatus according to the present invention, said physical characteristics measured by said measuring device is a bioelectric impedance value, and said condition of the living body evaluated by said arithmetic and control device is of concerning to a body fat.

In accordance with still another aspect of the present invention, a bio-characteristic value measuring apparatus comprises an input and display device, a storage device, a measuring device, and an arithmetic and control device, in which:

said input and display device inputs a personal body data of a test subject and indicates said inputted personal body data, evaluated result and the like;

said storage device stores said inputted personal body data of the test subject;

said measuring device measures a physical characteristics of a living body; and said arithmetic and control device evaluates a condition of the living body of the test subject based on said physical characteristics and the inputted personal body data;

wherein said input and display device is a LCD of touch panel type which is designed such that, upon setting the personal body data, a display area available for input operation lights up or flashes.

There will now be described in detail preferred embodiments of the present invention with reference with the accompanying drawings.

DETAILED DESCRIPTION OF THE PREFERRED EMBODIMENTS

A bio-characteristic value measuring apparatus according to the present invention employs a configuration in which a luminescent element corresponding to a switch allowing a key entry is turned on when a personal body data of a test subject is inputted.

Further, the bio-characteristic value measuring apparatus according to the present invention employs a configuration in which a standby period of automatic power-off function which automatically turns off a power supply of the bio-characteristic value measuring apparatus is adaptively changed in response to the age data entered when the personal body data of the test subject is inputted.

Still further, the bio-characteristic value measuring apparatus according to the present invention employs a configuration in which upon setting the personal body data of the test subject, the age data is set first among the body information.

As an embodiment of a bio-characteristic value measuring apparatus according to the present invention, a body fat meter will be described with reference to the attached drawings.

Figure 1:
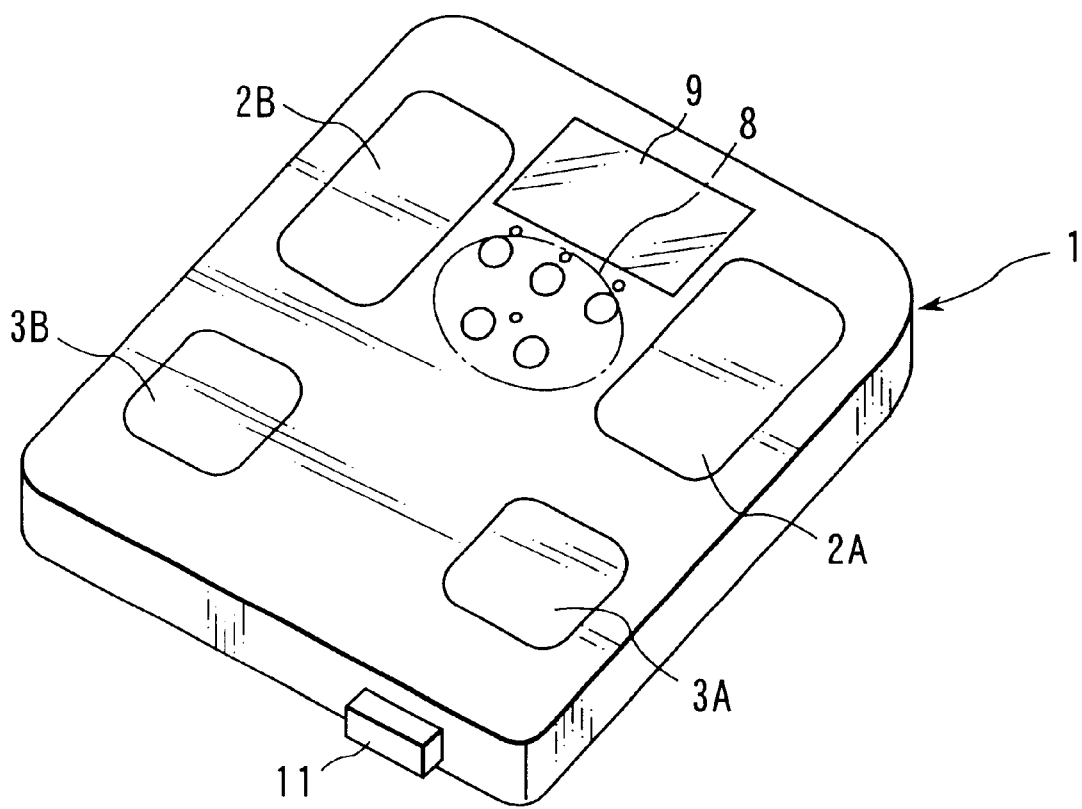
FIG. 1 is a general perspective view of a body fat meter of an embodiment according to the present invention.
Figure 2:
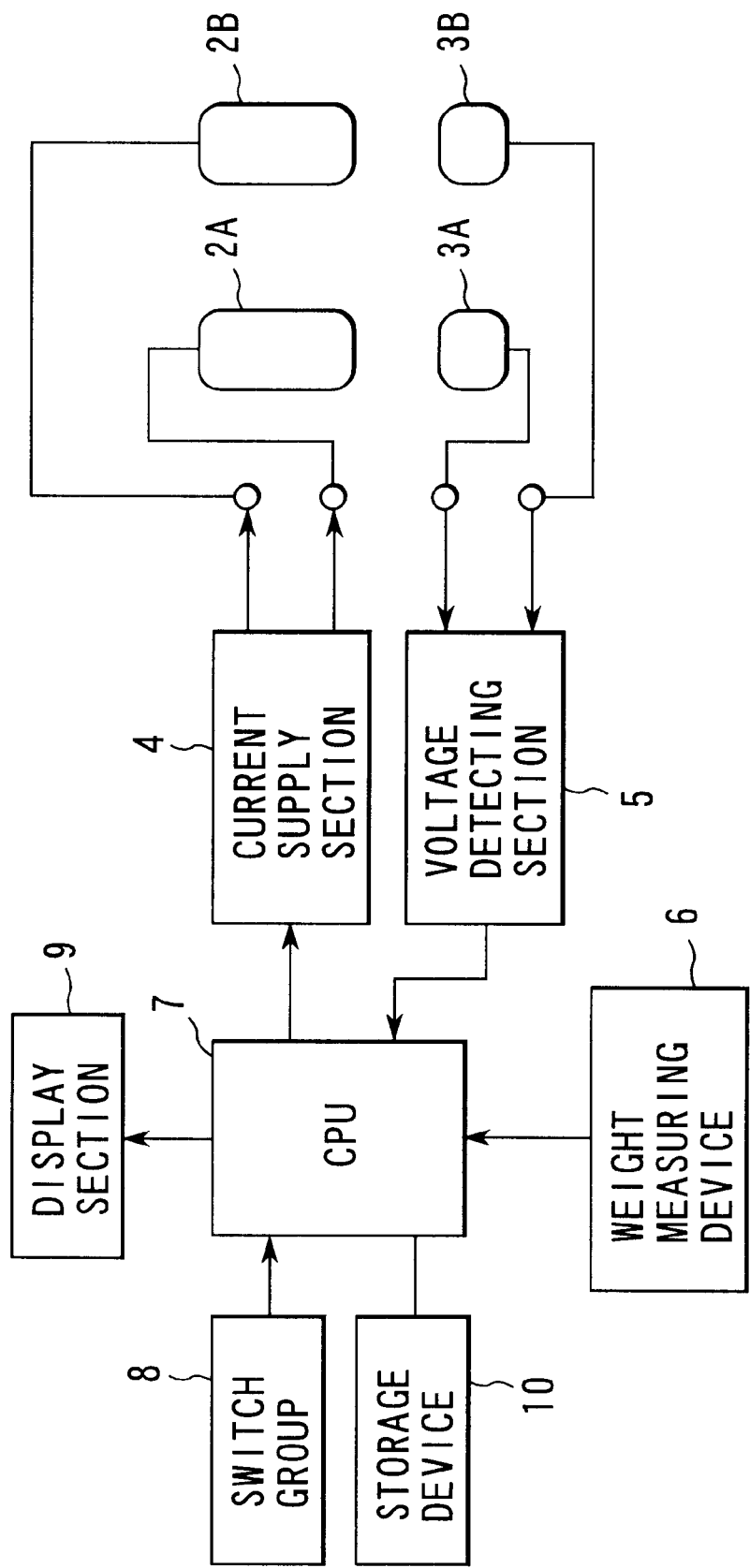
FIG. 2 is an electrical block diagram of the body fat meter of an embodiment according to the present invention.

FIG. 1 is a general perspective view of a body fat meter of an embodiment according to the present invention. FIG. 2 is a block diagram illustrating an electrical connection in said body fat meter.

On the top surface of a body fat meter main body 1, is provided a plurality of electrodes 2A, 2B, 3A and 3B. A pair of electrodes 2A and 2B is connected to a current supply section 4 for applying a weak constant current at high frequency into a body to allow the impedance between feet to be measured. Another pair of electrodes 3A and 3B is connected to a voltage detecting section 5 for measuring the amount of voltage drop in said constant current. It should be noted that the electrodes 2A and 3A would be brought into contact with right foot and the other electrodes 2B and 3B with left foot.

Still further, the body fat meter main body 1 is equipped with a weight measuring device 6 disposed therein integrally, which serves as a weight measuring means for measuring the weight applied thereto, that is, the body weight of a test subject, when the test subject steps on the body fat meter main body 1. This voltage measuring circuit 5 and the weight measuring device 6 are connected to a CPU 7 served as an arithmetic and control means for making control and arithmetic operation for the whole unit of the body fat meter. To this CPU 7 are connected; a group of switches 8 served as a setting means which is pressed upon starting of a measurement; a display section 9 served as a display means for indicating the body fat percentage and the body weight determined by the CPU 7 and the contents of the set personal data; and a storage device 10 served as a storage means for storing the set personal body data and the measured value. Further, in near side of the body fat meter main body 1 is arranged a measuring switch 11, one of the group of switches 8, to be pressed upon measuring to start the measurement of the body fat percentage.

Figure 3:
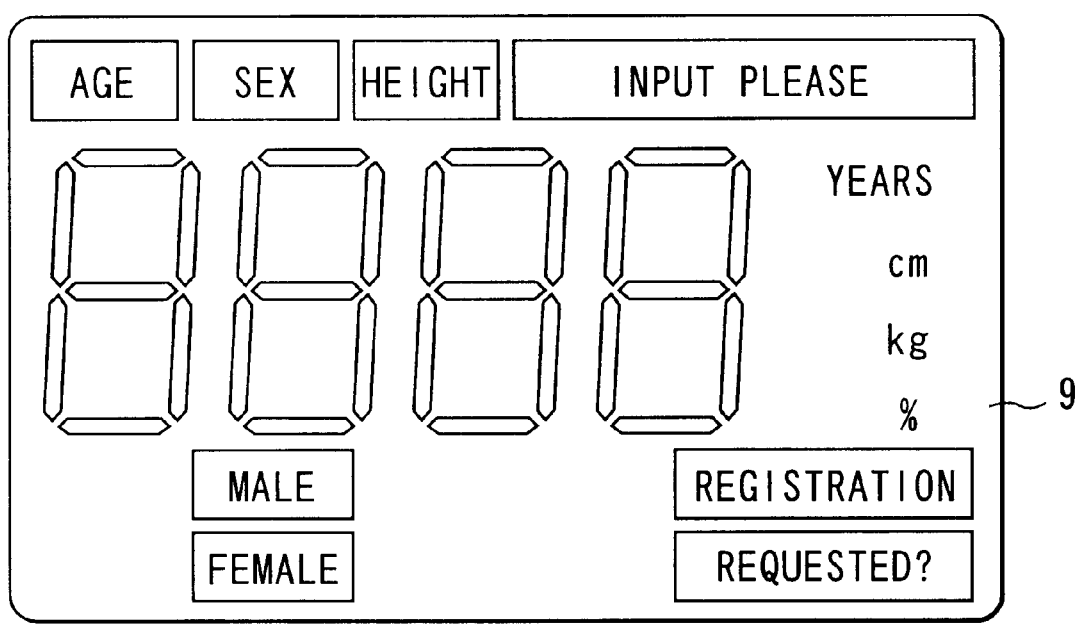
FIG. 3 is a schematic plan view of a display section and a switch section of the body fat meter of an embodiment according to the present invention.
Figure 3:
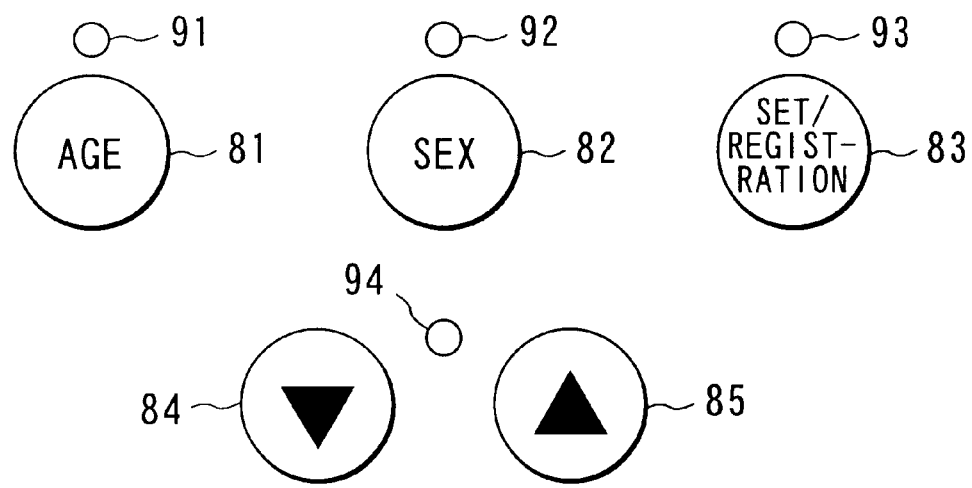

FIG. 3 is an enlarged plan view of the components concerned, in the display section 9 and the group of switches 8.

The display section 9 is a LCD, which includes a message display section for indicating a set of messages when a personal body data being set and a numeric value display section capable of indicating a set value and a measured value and the likes. Under this LCD is arranged a group of setting keys, including an age key 81, a sex key 82, a set/register key 83, a down key 84 and an up key 85. Correspondingly to each of these keys is arranged a plurality of LEDs 91 to 94 served as luminescent elements therefor.

Figure 4:
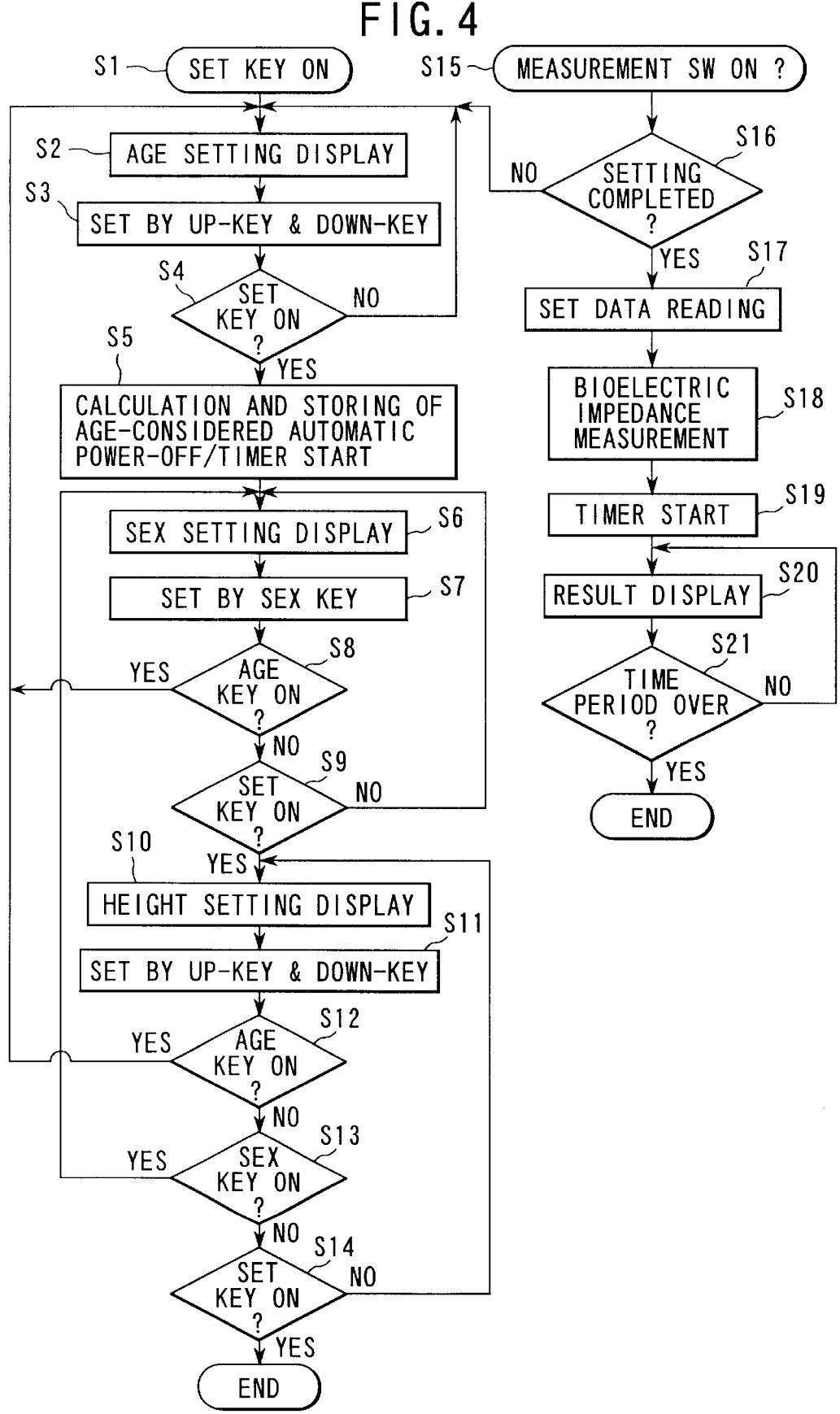
FIG. 4 is a flow chart illustrating a flow of setting and measuring operation of the body fat meter of an embodiment according to the present invention.
Figure 5A:
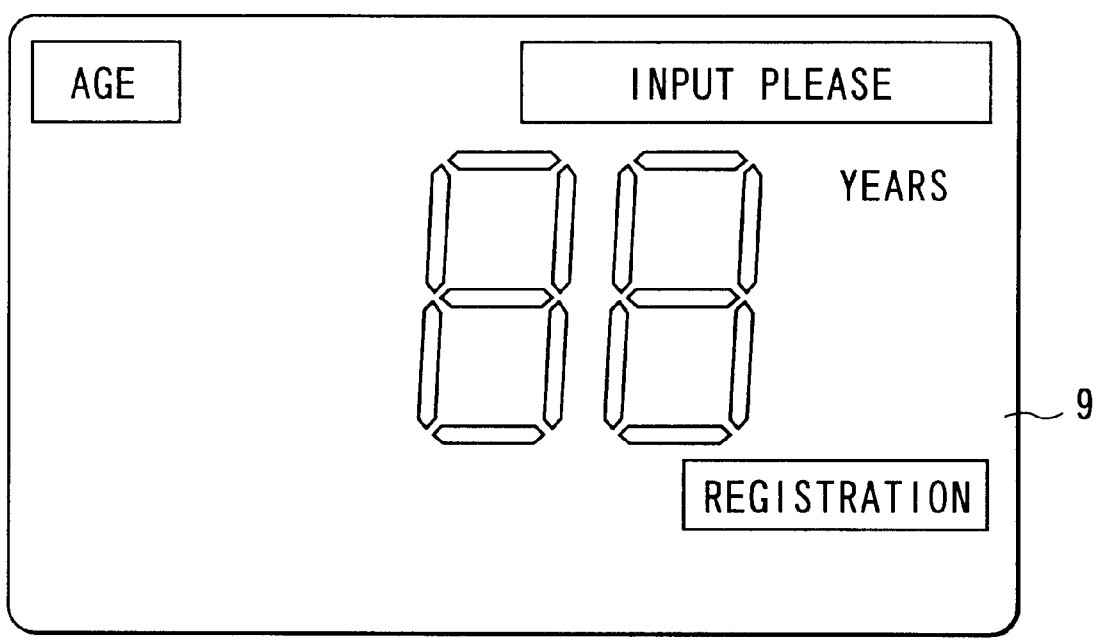
FIGS. 5(a), 5(b), and 5(c) are an enlarged plan view of the components concerned in the body fat meter of an embodiment according to the present invention, illustrating a display transition of the setting condition.
Figure 5A:
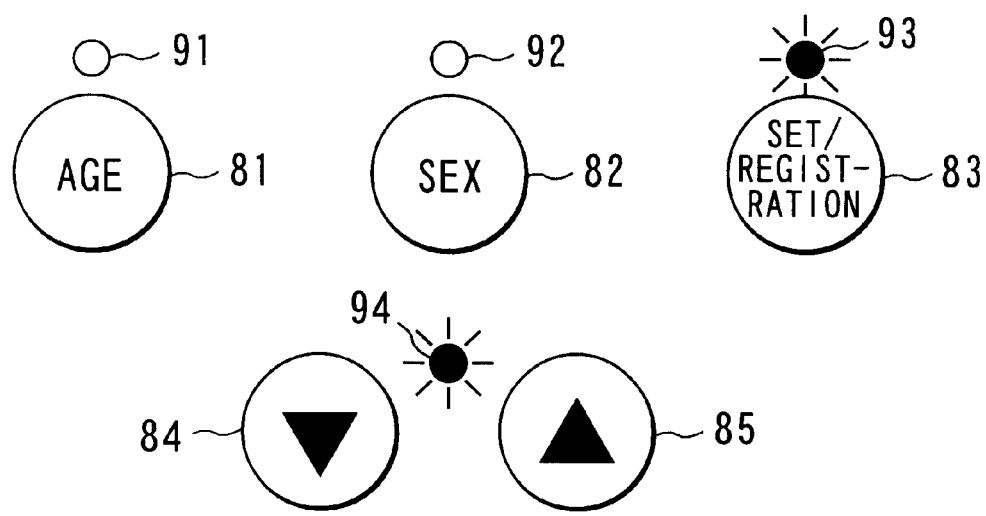
Figure 5B:
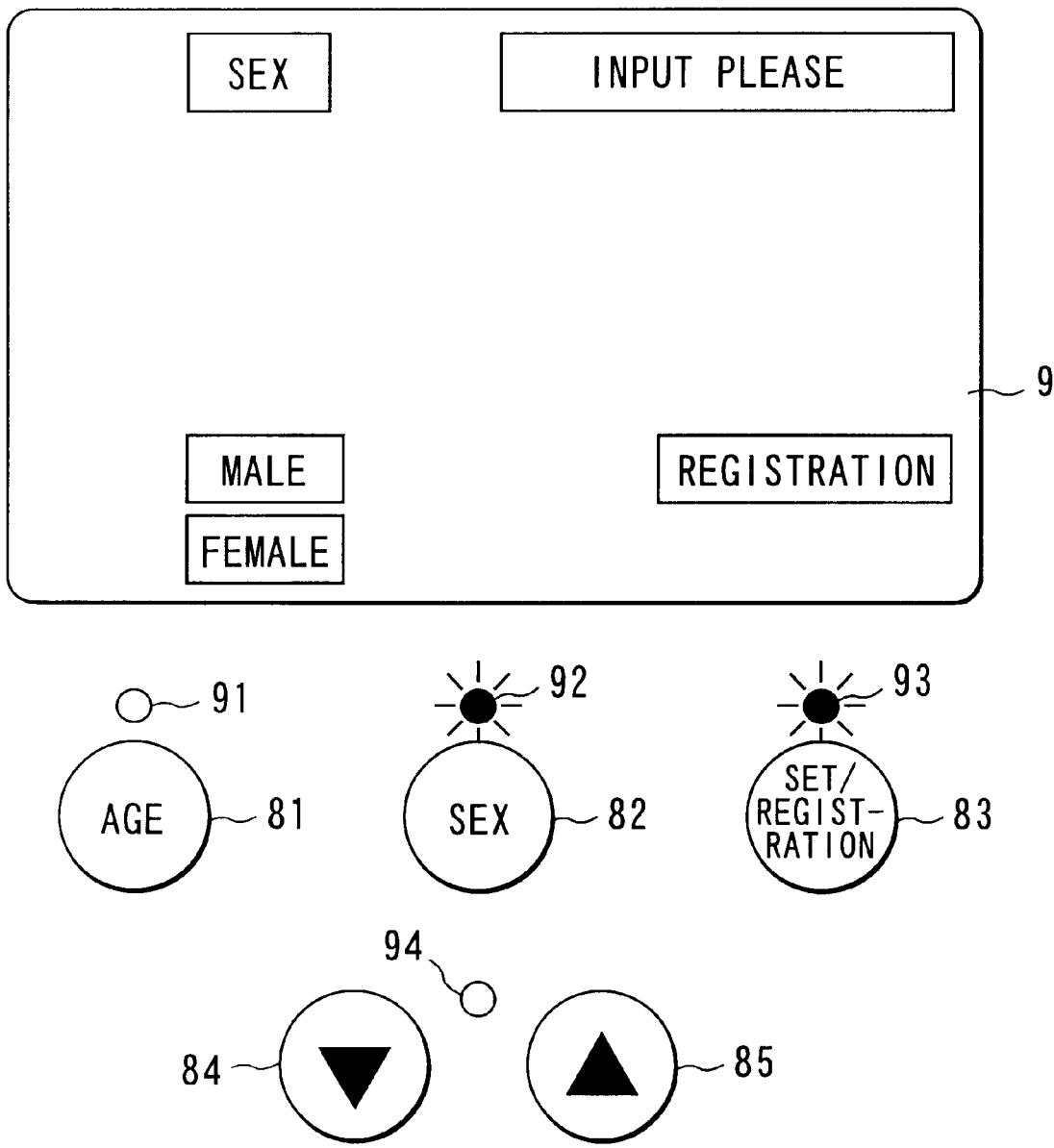
Figure 5C:
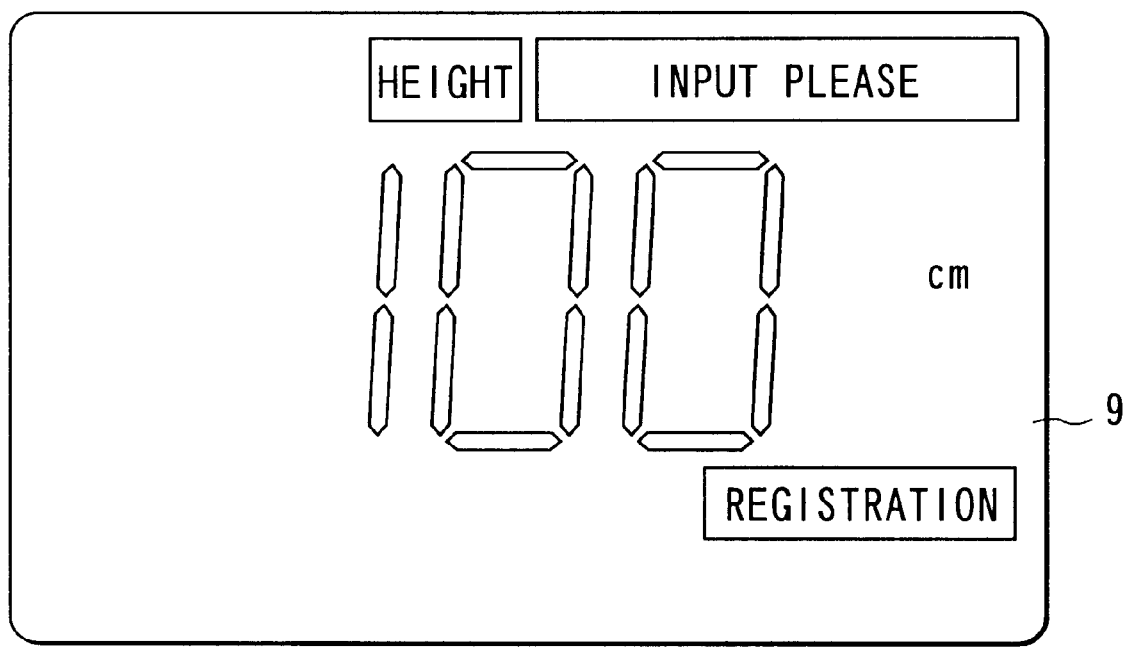
Figure 5C:
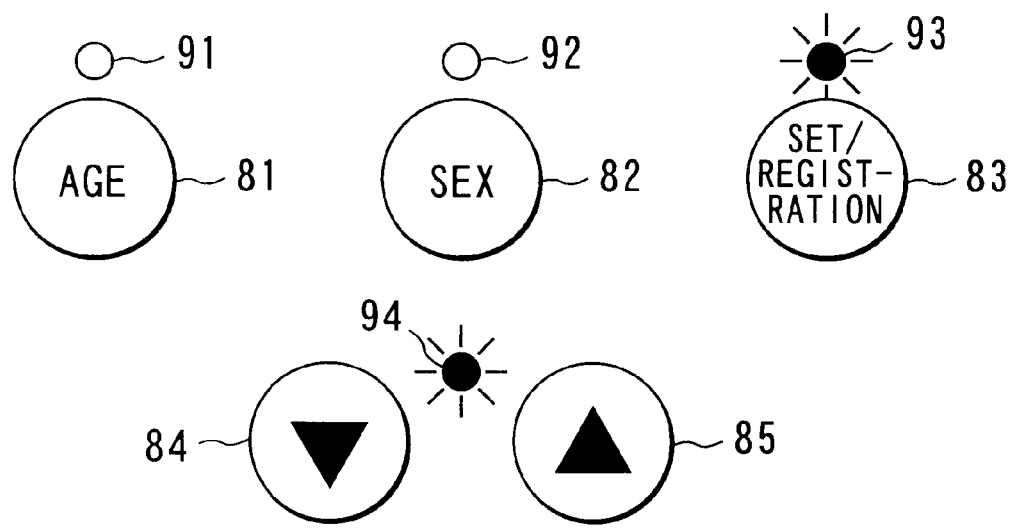

Following the description about the components, the flow of setting procedure of a personal body information in the present body fat meter will now be described with reference to the flow chart in FIG. 4 and the enlarged plan view of the components concerned in FIGS. 5(a)–5(c), illustrating a display transition of setting condition.

The description herein is made on the case where a 50-year-old female of 160 cm tall sets the data.

When the set/register key 83 is pressed, the LED corresponding to the key 83 is also lighted up to bring the body fat meter into a mode for setting a personal body data (step S1). In setting mode, the display section 9 displays a message for requesting her to set her age as shown in FIG. 5(a), and at the same time the LED 91 corresponding to the age key 81 is also lighted up (step S2). Herein, since the test subject uses the down key 84 and the up key 85 to change the age value, the LED 94 corresponding to these keys is also lighted up. The test subject sets the display to be 50, which is her age (step S3). The CPU 7 in turn determines whether or not the set/register key 83 has been pressed, and if the key 83 has been pressed, then the set age will be stored in the storage unit 10, but if the key 83 has not been pressed, the process returns to the step 2 to make the display for requesting age setting kept indicated (step S4).

When the age has been stored in the storage device 10, the CPU 7 determines a standby time until the automatic power-off, taking the age into consideration. The automatic power-off standby time is calculated and set, as defined herein by: the ten's place of the numeric figures of age×30 (seconds)= the automatic power-off standby time. Since currently the age 50 has been set, therefore 2.5 minutes, defined as 5×30=150 (seconds), would be set. At the same time when the standby time is set, the timer in the CPU 7 starts to measure the time until the automatic power-off. This timer is driven in the background of the CPU 7 separately from the flowchart in FIG. 4, and if there is no key entry occurred in the following 2.5 minutes in the setting modes, then the power supply is to be turned off automatically. That is, each key entry resets the timer to measure another period of 2.5 minutes (step S5).

When the age has been set, the LED 91 corresponding to the age key 81 is put out and the display section 9 displays the message for requesting the test subject to set a sex as shown in FIG. 5(b), and at the same time the LED 92 corresponding to the sex key 82 is lighted up (step S6). The test subject presses the sex key 82 to change the sex indicated on the display section 9. In this example, female is selected (step S7). At this moment, it is determined whether or not the age key 81 is being pressed, and if so, it should be determined that the wrong age data has been entered, and the process returns to step 2 to allow the test subject to set the age again (step S8). Subsequently, the process determines whether or not the set/register key 83 has been pressed or not, and if the key 83 has been pressed, the set sex is stored in the storage device 10, and contrarily if the key 83 has not been pressed, then the process returns to the step 6 to be kept in the indicating state for requesting the setting of the sex (step S9).

When the sex has been set, the LED 92 corresponding to the sex key 82 is put off, the display section 9 displays another message for requesting the test subject to set the height as shown in FIG. 5(c), and at the same time the LED 94 corresponding to the down key 84 and the up key 85 is lighted up (step S10). The test subject uses the down key 84 and the up key 85 to change the height value. In this example, the test subject sets the value to be 160, which is her height (step S11). At this moment again, it is determined whether or not the age key 81 is being pressed, and if so, then it is determined the wrong age has been set and the process returns back to step 2 to allow the user to set the age again (step S12). Further, it is also determined whether or not the sex key 82 is being pressed, and if so, then it is determined the wrong sex has been set and the process returns back to step 6 to allow the user to set the sex again (step S13). Then, it is determined whether or not the set/register key 83 has been pressed, and if pressed, then the set height is stored in the storage device 10, but if not pressed, then the process returns back to step S10 to make the display for requesting the test subject to set the height kept indicated (step S14). When the height has been set, it is determined that all of the setting has been completed to end the setting mode.

Then the flow in measuring the body fat percentage will be described with reference to the flow chart in FIG. 4.

When the measurement switch 11 is pressed, the body fat meter main body 1 is powered on (step S15) to determine whether or not the personal body data has been set. At that time, if the personal body data has not been set, the process is automatically transferred into the setting mode of step S2 to set the data sequentially, beginning from the age data (step S16).

When the personal body data has been set, the CPU 7 reads the personal body data out of the storage device 10. At that time, the age of the test subject is also read, and a standby time until the automatic power-off for the result display is determined similarly to that in the setting mode. It should be noted that, since what is necessary for the standby time is a time period available exclusively for grasping the indicated body fat percentage and body weight values, the display is not required to be indicated for minutes as in the setting mode even in the case that the test subject is an elderly person, but the standby time is preferably adapted to be changed within the range, which is shorter than that in the setting mode, to meet the certain level of automatic power-off standby time taking the age of the test subject into consideration. Herein, the standby time is defined by: the ten's place of the numeric figures of age×5 (seconds)=the automatic power-off standby time. That is, since the stored age is 50-year-old, then the standby time is defined as and set to 5×5=25 (seconds) (step S17).

The test subject steps on the body fat meter to bring the respective electrodes 2A, 2B, 3A and 3B into contact with the bottom of feet, and at the same time when the weight measuring device 6 detects the weight, the body fat meter starts to measure the bioelectric impedance. The CPU 7 calculates a body fat percentage based on the measured bioelectric impedance value and the stored body data of the test subject. At the same time, the body weight is also measured (step S18).

When the body fat rate of the test subject has been calculated, the timer within the CPU 7 is activated to measure the set time period until the automatic power-off (step S19). As the timer is activated, the display section 9 indicates the evaluated results of body fat rate and body weight (step S20). The timer herein determines whether or not the time period is over, and if the time period is not past, the process returns to the step S20 to make the result display kept indicated, but if the time period has been past, then the display is disappeared to end the process.

There has been described above an embodiment of the bio-characteristic value measuring apparatus according to the present invention, in which the age, the sex and the height are set as the personal setting items, but the setting items are not limited to these ones but may be varied adaptively so as to set whether or not the test subject is an athlete, or to set the race of the subject, or the apparatus may alternatively store a plural sets of the personal data for a plurality of test subjects.

As for the location of a luminescent element corresponding to the personal body data input section, although the LED is located above the entry key in the configuration of the above embodiment, the luminescent element may be arranged inside the entry key, or a letter is emerged out by luminescence of the luminescent element disposed inside the key.

Still further, although the described embodiment has employed the LCD as a display device and a plurality of switches as an input device, a LCD of touch panel type may be employed, which comprises a integrated single unit of display device and input device. In this case, upon setting the personal body data, a plurality of switches may be displayed on the LCD of touch panel type with some of them being emphasized by lighting or flashing to indicate the display area of touching section available for entry so as to allow the user to recognize the data available for entry.

Further, although in the above embodiment, a standby time until an age-considered automatic power-off has been set based on the entered age, the age is not necessarily entered directly but any data may be available for setting so far as the data could be used to estimate the age, including, for example, a date of birth, in which case the age is determined by an arithmetic means.

Still further, although in the above embodiment, the standby time until the age-considered automatic power-off in the setting of the personal body data has been exemplary defined as the ten's place of the age of a test subject×30 (seconds), it is not necessarily limited thereto but the standby time may be constant until the age of 40-year-old, and for the setting of the age over 40, the standby time may be varied depending on the set age, that is, the standby time could be adaptively varied to meet the user's convenience with the current consumption of the available batteries and circuit into account.

Further, although in the body fat meter of the above embodiment, the method for measuring the bioelectric impedance between the feet has been described, since the present invention relates to a method for setting the personal body data in the body fat meter, the method is not necessarily limited to this but the body fat meter may be of the type for measuring the bioelectric impedance between the hands or between a hand and a foot, or for measuring the body fat rates in respective regions by the combination of the above measurements.

Yet further, although the bio-characteristic value measuring apparatus of the above embodiment has focused on a body fat meter, since the present invention is applicable to any devices for evaluating and indicating a condition of a living body based on the entered information of the personal body data and the measured physical-characteristic value of the living body, therefore the application is not limited to the body fat meter.

Since, when the bio-characteristic value measuring apparatus according to the present invention is used, a luminescent element corresponding to a switch available for key entry is lighted up upon setting the personal body data, a user can easily recognize the key to be pressed, so that the user is guided by the light to successively input respective body data in order, allowing the setting to be facilitated.

Further, a body fat meter, in which a standby time of the automatic power-off system is designed to be modified in response to the age, allows the standby time for the automatic power-off to be modified by using a parameter of the age as set in a typical body fat meter, without requesting the user to make a special setting operation. Thereby, for example, the older the user is, the longer time period until the automatic power-off could be set, so that upon setting the personal body data, even the person of poor at machine operation could perform the setting operation slowly, thus to reduce a risk such as the power-off in the course of setting operation and the improper measurement of the body fat possibly caused by the improper setting of the personal body data. Still further, upon measuring the body fat, even the elderly person could take longer time to recognize a display, and thus the user could have sufficient time to judge a variation of the body fat, allowing a user-friendly operation.

Yet further, by employing a configuration in which upon setting the personal body data, the age is set first among the setting items, once an entry of the age has been done, the standby time may be modified immediately in response to the set age, so that the modified standby time for the automatic power-off could be available even in the following setting operation, which makes the setting operation more user-friendly.

What is claimed is:

1. A bio-characteristic value measuring apparatus comprising an input device, a storage device, a measuring device, an arithmetic and control device; and a display device, in which:

said input device inputs personal body data of a test subject;

said storage device stores said inputted personal body data;

said measuring device measures physical characteristics of a living body;

said arithmetic and control device evaluates a condition of the living body of the test subject based on said physical characteristics and said inputted personal body data to produce an evaluated result; and said display device indicates the inputted personal body data and evaluated result;

wherein said input device comprises a plurality of switches, each switch having a luminescent element associated therewith and located in the vicinity of or inside the switch; and wherein the luminescent element associated with one of the switches available for an entry operation to set the personal body data can be illuminated.

2. A bio-characteristic value measuring apparatus in accordance with claim 1, in which said physical characteristics measured by said measuring device is a bioelectric impedance value, and said condition of the living body evaluated by said arithmetic and control device is of concerning to a body fat.

3. A bio-characteristic value measuring apparatus comprising an input device, a storage device, a measuring device, an arithmetic and control device, and a display device, in which:

said input device inputs personal body data of a test subject;

said storage device stores said inputted personal body data;

said measuring device measures physical characteristic of a living body;

said arithmetic and control device evaluates a condition of the living body of the test subject based on said physical characteristics and said inputted personal body data to produce an evaluated result; and said display device indicates the inputted personal body data and evaluated result;

wherein said input device comprises a plurality of switches, each switch having a luminescent element associated therewith and located in the vicinity of or inside the switch; and wherein the luminescent element associated with one of the switches available for an entry operation to set the personal body data can be illuminated; and said display device, upon setting the personal body data, specifies data to be entered in an entry operation.

4. A bio-characteristic value measuring apparatus comprising an input device, a storage device, a measuring device, an arithmetic and control device, and a display device, in which:

said input device inputs personal body data of a test subject including an age data;

said storage device stores said inputted personal body data;

said measuring device measures physical characteristics of a living body;

said arithmetic and control device evaluates a condition of the living body of the test subject based on said physical characteristics and said inputted personal body data to produce an evaluated result; and said display device indicates the inputted personal body data and evaluated result;

wherein said arithmetic and control device modifies a standby time until an automatic power-off based on the entered age data.

5. A bio-characteristic value measuring apparatus in accordance with claim 3, in which the data to be inputted first among the personal body data from said input device is a data concerning to the age.

6. A bio-characteristic value measuring apparatus in accordance with claim 5, in which said arithmetic and control device modifies the standby time until the automatic power-off to become longer as the entered age gets higher.

7. A bio-characteristic value measuring apparatus comprising an input device, a storage device, a measuring device, an arithmetic and control device, and a display device, in which:

said input device inputs personal body data of a test subject including an age data;

said storage device stores said inputted personal body data;

said measuring device measures physical characteristics of a living body;

said arithmetic and control device evaluates a condition of the living body of the test subject based on said physical characteristics and said inputted personal body data to produce an evaluated result; and said display device indicates the inputted personal body data and evaluated result;

wherein in said input device, upon setting the personal body data, a luminescent element corresponding to a section available for an entry operation is lighted up; and said arithmetic and control device modifies a standby time until an automatic power-off based on the entered age data.

8. The bio-characteristic value measuring apparatus of claim 7, wherein said input device comprises a plurality of switches, each switch having a luminescent element associated therewith and located in the vicinity of or inside the switch; and wherein the luminescent element associated with one of the switches available for an entry operation to set the personal body data can be illuminated.

9. A bio-characteristic value measuring apparatus comprising an input and display device, a storage device, a measuring device, and an arithmetic and control device, in which:

said input and display device inputs personal body data of a test subject;

said storage device stores said inputted personal body of the test subject;

said measuring device measures physical characteristics of a living body; and said arithmetic and control device evaluates a condition of the living body of the test subject based on said physical characteristics and the inputted personal body data to produce an evaluated result;

said input and display device indicates said inputted personal body data and said evaluated result;

wherein said input and display device is a LCD of touch panel type which is designed such that a display area of a touching section of the LCD available for an entry operation to set the personal body data lights up or flashes.

* * * * *